United States Patent [19]

Bailey et al.

[11] Patent Number: 5,416,008
[45] Date of Patent: May 16, 1995

[54] CROSS-REGULATION OF GENE EXPRESSION IN RECOMBINANT CELLS

[75] Inventors: James E. Bailey; Wilfred Chen; Pauli Kallio, all of Pasadena, Calif.

[73] Assignee: California Institute of Technology, Pasadena, Calif.

[21] Appl. No.: 770,100

[22] Filed: Oct. 1, 1991

[51] Int. Cl.$^6$ .............. C12N 15/00; C12N 1/19; C12N 1/21; C12N 15/09
[52] U.S. Cl. .................. 435/691; 435/71.1; 435/71.2; 435/172.3; 435/252.33; 435/254.21
[58] Field of Search ............ 435/240.2, 252.3, 252.33, 435/255, 256, 69.1, 70.3, 71.1, 71.2, 172.3, 254.21

[56] References Cited

FOREIGN PATENT DOCUMENTS 0136907 4/1985 European Pat. Off. ...... C12N 15/00

OTHER PUBLICATIONS

Amann, E. and Brossius, J., "'ATG vectors' for regulated high-level expression of cloned genes in *E. coli*," *Gene*, 40, pp. 183-190 (1985).

Amann, E. et al., "Vectors bearing a hybrid trp-lac promoter useful for regulated expression of cloned genes in *Escherichia coli*," *Gene*, 25, pp. 167-178 (1983).

Backman, K. and Ptashne, M., "Maximizing Gene Expression On A Plasmid Using Recombination In Vitro," *Cell*, 13, pp. 65-71 (1978).

Bailey, J. W. and Ollis, D. F., *Biochemical Engineering Fundamentals*, pp. 307-372 (1986).

Chen, W. et al., "Molecular Design of Expression Systems: Comparison of Different Repressor Control Configurations Using Molecular Mechanism Models", *Biotech. and Bioengin.*, 38, pp. 678-687 (1991).

Crowl, R. et al., "Versatile expression vectors for high-level synthesis of cloned gene products in *Escherichia coli*", *Gene*, 38, pp. 31-38 (1985).

Goeddel, D. V. et al., "Expression in *Escherichia coli* of chemically synthesized genes for human insulin," *Proc. Nat. Acad. Sci. U.S.A.*, pp. 106-110 (1978).

Gorman, J. A. et al., "Regulation Of The Yeast Metallothionine Gene," *Gene*, 48, pp. 13-22 (1986).

Hadcock, J. R. et al., "Cross-regulation between G--Protein-mediated Pathways", *J. Biol. Chem.*, 266: pp. 11915-11922 (1991).

Hadcock, J. R. et al., "Cross-regulation between G--Protein-mediated Pathways", *J. Biol. Chem.*, 265, pp. 14784-14790 (1990).

Kaufmann, R. J., "High Level Production Of Proteins In Mammalian Cells," *Genetic Engineering: Principles and Methods*, 9, pp. 155-198 (1987).

Kramer, R. A. and Andersen, N., "Isolation of yeast genes with mRNA levels controlled by phosphate concentration," *Proc. Nat. Acad. Sci. U.S.A.*, 77, pp. 6541-6545 (1980).

Lee, S. B. and Bailey, J. E., "Genetically Structured Models for lac Promoter-Operator Function in the *Escherichia coli* Chromosome and in Multicopy Plasmids: lac Operator Function" *Biotech. and Bioeng.*, XXVI, pp. 1372-1378 (1984).

(List continued on next page.)

*Primary Examiner*—Richard A. Schwartz
*Assistant Examiner*—Nancy T. Vogel
*Attorney, Agent, or Firm*—Graham & James

[57] ABSTRACT

Recombinant cells providing for the controlled expression of product proteins by way of cross-regulation between interacting operons. A structural gene for a product protein and a structural gene for a repressor of a second operon are included in a first operon. A protein encoded by a structural gene of the second operon is a repressor of the first operon. The second operon may reside on a plasmid or a chromosome of the host cell. The present invention provides for controlled expression of product protein over a range of copy numbers, as well as high transcription efficiency in the induced state. The invention includes methods for the controlled expression of product protein by recombinant cells.

15 Claims, 6 Drawing Sheets

OTHER PUBLICATIONS

Lee, S. B. and Bailey, J. E., "Genetically Structured Models for lac Promoter-Operator Function in the Chromosome and in Multicopy Plasmids: lac Promoter Function", *Biotech. and Bioengin.*, XXVI, pp. 1383–1389 (1984).

Moser, D. R. and Campbell, J. L., "Characterization and Complementation of pmB1 Copy Number Mutant: Effect of RNA I Gene Dosage On Plasmid Copy Number and Incompatibility," *J. Bacteriol.*, 154, pp. 807–818 (1983).

Neumann, J. R. et al., "A Novel Rapid Assay for Chloramphenicol Acetyltransferase Gene Expression", *Biotechniques*, 5, 444–47 (1987).

Oshima, Y., "Regulatory Curcuits for Gene Expression: The Metabolism of Galactose and Phosphate" in *The Molecular Biology of the Yeast Saccharomyces: Metabolism and Gene Expression*, J. Strathern et al. eds. (1982).

Platt, T., "Regulation of Gene Expression in the Tryptophan Operon of *Escherichia coli,*" in J. H. Miller, and W. S. Resinikoff, eds. *The Operon* (1975).

Ptashne, M., "Repressor and Its Action, " in *The Bacteriophage Lambda*, A. D. Hershey ed. (1971).

Seo, J-H and Bailey, J. E., "Effects of Recombinant Plasmid Content on Growth Properties and Cloned Gene Product Formation in *Escherichia coli*, *Biotech. and Bioengin.*, " XXVII, pp. 1668–1674 (1985).

Sledziewski, A. J. et al., "Construction of Temperature-Regulated Yeast Promoters Using the MATλ2 Repression System," *Biotechnology*, 6, pp. 411–416 (1988).

Windass, J. D., et al., "The constitution of a synthetic *Escherichia coli* trp promoter and its use in the expression of a synthetic interferon gene," *Nucl. Acids Res.*, 10, pp. 6639–6657 (1982).

FIG. 5

Primer I and II used for the amplification of lacI gene

LacI

Primer I SEQ. ID NO. 1

```
        BspEI                    SD          Start
  5'      |                                    ↱
   GCGATTCCGGATTAGCAATTCAGGGTGGTGAATGTGAAAC
              |
```

Primer II SEQ. ID NO.2

```
        BspEI                  trpA tran. stop
  5'      |
   GCTAATCCGGAATCGCAAAAAAAAGGGGGGTGATTAGGGGGGGT
   GCGTTACGCTCACTGCCCGCTTTCCAGTCGG
       Stop
```

Template: pMJR1560

FIG. 6

Primer III and IV used for amplification of cI gene

Primer III SEQ. ID NO. 3

```
     ECORI  Start
            ↱
  5' GGGAATTCATGAGCACAAAAAAGAAACCAT
           |

10987654321
    AGGAAACAGAATTCATG
      SD
```

Primer IV SEQ. ID NO. 4

```
        Pst1
  5'     |
    GCTGCAGCTTATCAGCCAAACGTCTCTTCA
         |
           Stop
```

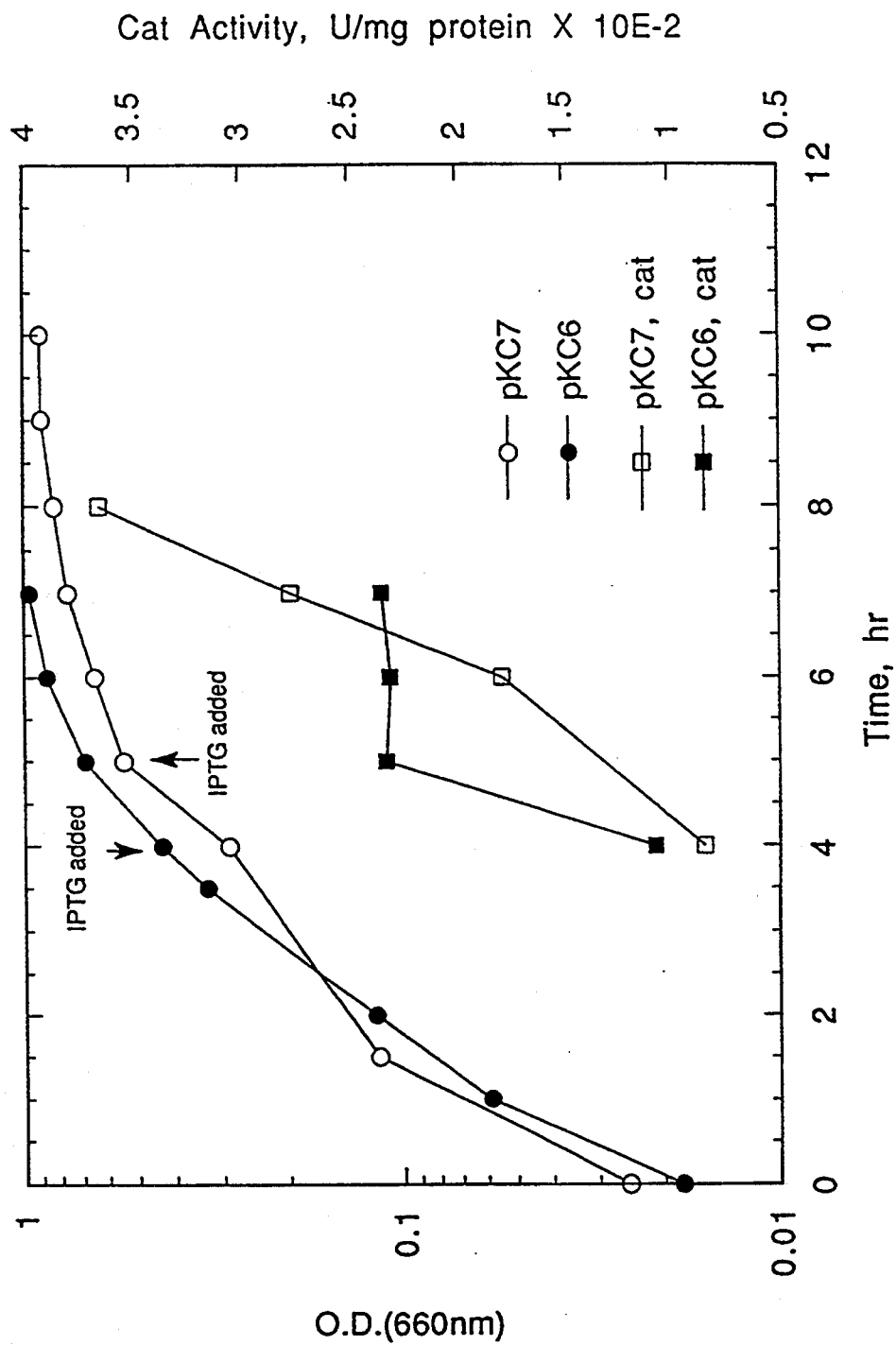
FIG. 7 Comparison of growth and CAT activity for pKC6 and pKC7

CROSS-REGULATION OF GENE EXPRESSION IN RECOMBINANT CELLS

This invention relates to improvements in the control of gene expression in recombinant cells. More particularly, this invention relates to the control of gene expression in recombinant cells whereby transcription is regulated by a pair of interacting promoter-operator systems, a construct referred to herein as cross-regulation. This invention also relates to methods for controlling the expression of a product protein in recombinant cells by cross-regulation.

BACKGROUND OF THE INVENTION

Recombinant DNA technology revolutionized the fields of biochemistry and molecular biology over the past decade. It is now possible to produce proteins, heretofore available only in trace amounts, in commercial quantities by transforming bacteria with nucleotide sequences encoding the desired protein. Efficient application of this technology to the commercial production of pharmaceuticals and other valuable substances requires that the production of the desired product be optimized.

In recombinant bacteria, for example, the transforming sequences are usually inserted into plasmids—extrachromosomal rings of double-stranded DNA. Bacteria transformed with these recombinant plasmids produce the protein encoded by transforming sequences ("product protein") in substantial yields.

The product protein is often heterologous; that is, it does not occur naturally in the host. Because the rate at which product protein is synthesized is generally limited by the quantity of messenger RNA ("mRNA") transcribed from the transforming DNA, the rate at which product protein is synthesized may be increased by increasing the number of transforming sequences per host cell. The number of such sequences is referred to herein as copy number.

In order to maximize product synthesis, bacterial host cells are transformed with many plasmids harboring the transforming sequence. Typically, the number of such plasmids ranges from 20 to 30 vectors per host cell. Copy number may also be increased by inserting multiple copies of a transforming sequence into each plasmid. See e.q., D. R. Moser and J. L. Campbell, 1983, "Characterization and Complementation of pMB1 Copy Number Mutants: Effect of RNA1 Gene Dosage on Plasmid Copy Number and Incompatibility", *J. Bacteriol.*, 154:809–181.

However, simply increasing the quantity of transcript is not sufficient to optimize protein synthesis by transformed cells. The product protein may be toxic, to varying degrees, to the host cell. Expression of the transforming sequences at high levels also generally reduces host cell viability because such expression usurps the synthetic machinery of the host.

Moreover, recombinant bacteria often lose the transforming plasmids over time, resulting in a mixture of productive and non-productive cells. Because of the metabolic burden imposed by replication and production of the product of the transforming sequences, over time a population of transformed cells is eventually overtaken by wild-type cells, either pre-existing or resulting from segregational instability, competing with the transformed cells for available nutrients in a bioreactor.

A generally useful strategy for addressing these limitations is to grow transformed cells to a high density, while suppressing synthesis of the product protein. After the transformed cells have been grown to the desired density, a production phase is initiated by induction or derepression of transcription of the structural gene for the product protein. It is therefore necessary to retain control of the promoter for the structural gene for the product protein during the growth phase, while providing a high rate of protein transcription following induction or derepression.

While outlined here in the context of recombinant bacteria, similar considerations apply to other recombinant cells such as yeast, fungi, and higher eukaryotic cells.

SUMMARY OF THE INVENTION

Recombinant cells providing for the controlled expression of product proteins by way of cross-regulation between interacting operons. A structural gene for a product protein and a structural gene for a repressor of a second operon are included in a first operon. A protein encoded by a structural gene of the second operon is a repressor of the first operon. The second operon may reside on a plasmid or a chromosome of the host cell. The present invention provides for controlled expression of product protein over a range of copy numbers, as well as high transcription efficiency in the induced state. The invention includes methods for the controlled expression of product protein by recombinant cells.

BRIEF DESCRIPTION OF THE DRAWINGS

FIG. 5 depicts the construction of primers 1 (SEQ. ID No. 1) and 2 (SEQ. ID No. 2) for amplification of the lacI gene.

FIG. 6 depicts the construction of primers 3 (SEQ. ID No. 3) and 4 (SEQ. ID No. 4) for amplification of the cI gene.

FIG. 7 compares the growth (circles) and production of chloramphenicol acetyltransferase (squares) of *E. coli* in which expression of the transforming sequence is constitutive (solid symbols) and controlled by cross-regulation (open symbols).

DETAILED DESCRIPTION OF THE INVENTION

Figure 1:
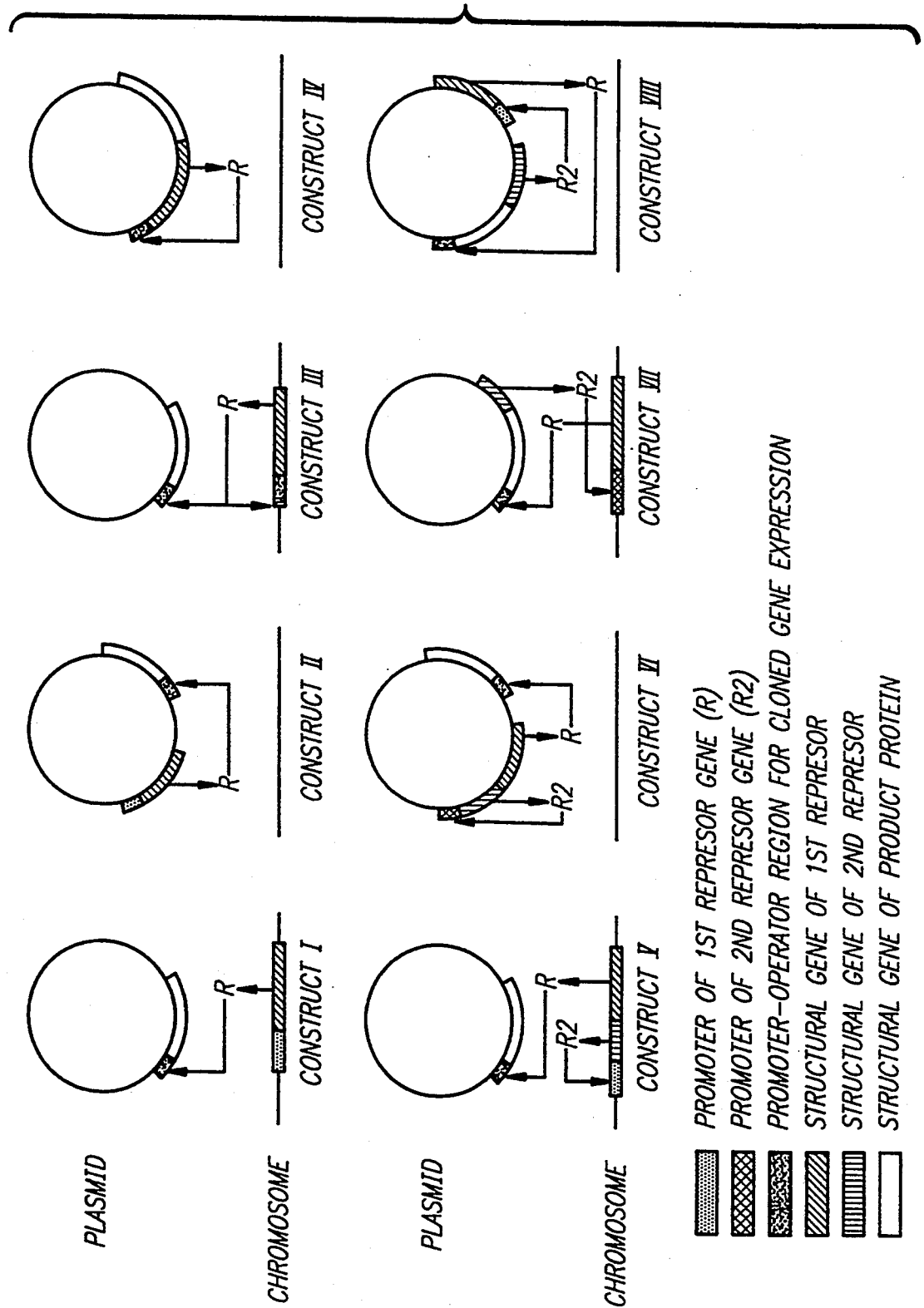
FIG. 1 is a schematic representation of the eight genetic constructs modeled in Example 1.

In order that the invention herein described may be more fully understood, the following detailed description is set forth. The following terms are employed in the specification:

Cloning—The process of obtaining a population of organisms or DNA sequences derived from one such organism or sequence by asexual reproduction.

DNA Sequence—A linear array of nucleotides connected one to the other by phosphodiester bonds between the 3' and 5' carbons of adjacent pentose moieties.

Expression—The process of producing a protein from a structural gene. Expression is a sequence of transcription followed by translation and, optionally, post-translational modification.

Inducer—A molecule that binds to a repressor with the result that the repressor does not bind to its operator.

Nucleotide—A monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is called a nucleoside. The base characterizes the nucleotide. The four DNA bases are adenine ("A"), guanine ("G"), cytosine ("C"), and thymine ("T"). The four RNA bases are A, G, C, and uracil ("U").

Operator—A sequence of nucleotides that controls and regulates transcription of genes, when functionally linked to those genes. Operators have been identified in, for example, the lac system (J. R. Beckwith and D. Ziper, eds., "The Lactose Operon" (1970)), the trp system (T. Platt, "Regulation Of Gene Expression In The Tryptophan Operon Of *Escherichia Coli*", in J. H. Miller and W. S. Reznikoff, eds., *The Operon* (1978)), the tac system (E. Amann et al., "Vectors Bearing A Hybrid Trp-lac Promoter Useful for Regulated Expression of Cloned Genes In *Escherichia Coli*", Gene, 25:167-78 (1983)), and trc system (E. Amann and J. Brosius, Gene, "'ATG Vector' for Regulated High-Level Expression of Cloned Genes in *Escherichia Coli*", 40:183-90 (1985)), as well as the major operator and promoter regions of phage λ (M. Ptashne, "Lambda Repressor And Its Action", in *The Bacteriophage Lambda*, A. D. Hershey, ed. (1971)). Operators occur in close physical proximity to, or are part of, a promoter.

Operon—A combination of DNA sequences comprising a promoter, possibly an operator, and one or more structural genes generally located 3' with respect to the promoter-operator sequence, such that the transcription of the structural genes is regulated by the promoter-operator sequence.

Plasmid—A nonchromosomal double-stranded DNA sequence replicated in a host cell. When a plasmid is inserted in a unicellular organism, the characteristics of that organism may be changed or transformed as a result of the DNA of the plasmid. For example, a plasmid carrying the gene for tetracycline resistance transforms a cell previously sensitive to tetracycline into one which is resistant to it. A plasmid harboring a transforming sequence is a "vector" for that sequence.

Promoter—A sequence of nucleotides which forms a site at which the enzyme RNA polymerase attaches to initiate transcription.

Protein—A linear array of amino acids connected one to the other by peptide bonds between the amino and carboxy groups of adjacent amino acids.

Recombinant DNA Molecule—A molecule consisting of segments of DNA from different genomes which have been joined end-to-end outside of living cells.

Repressor—A protein molecule that regulates transcription by binding to an operator sequence, and when bound, interferes with transcription.

Structural Gene—A DNA sequence which encodes a sequence of amino acids characteristic of a specific protein.

Transcription—The process of producing mRNA from a gene or DNA sequence.

Translation—The process of producing a protein from mRNA.

Termination Signal—A sequence of nucleotides that terminates transcription.

The present invention relates to the controlled expression of structural genes by recombinant cells. According to the present invention, expression of the product protein is suppressed by repressor molecules during propagation of the transformed cells. With expression thus repressed, transformed cells may be grown to high densities. When the effect of the repressor is removed, for example, by addition of an inducer, expression of the product protein occurs at a high rate. The present invention provides transformed cells whose expression of product protein is well controlled during the growth phase yet which express product protein at high yields upon induction or derepression.

According to the present invention, these characteristics are effected by controlling the expression of a product protein with a pair of interacting promoter-operator systems. A structural gene encoding the product protein is a component of a first operon, as is a structural gene which encodes a repressor for the promoter-operator of the second operon. A second operon includes a structural gene that encodes a repressor for the promoter-operator of the first operon. As demonstrated below, the present invention represents an improvement over prior art systems by providing a transformed host wherein control of expression of product protein is maintained over a range of copy numbers, while the expression of product protein in the induced state is improved.

A promoter is a sequence of nucleotides on a DNA strand to which the enzyme RNA polymerase binds to begin transcription. It is this binding that initiates the process of transcription; the rate of transcription is a function of the frequency with which the binding step occurs. An operator is a nucleotide sequence that may be part of a promoter, or 3' to the promoter, through which control of the transcription process is effected.

Several promoter-operator systems, such as lac, (D. V. Goeddel et al., "Expression in Escherichia Coli of Chemically Synthesized Genes for Human Insulin", *Proc. Nat. Acad. Sci. U.S.A.*, 76:106-110 (1979)); trp (J. D. Windass et al. "The Construction of a Synthetic *Escherichia Coli* Trp Promoter and Its Use In the Expression of a Synthetic Interferon Gene", *Nucl. Acids. Res.*, 10:6639-57 (1982)) and λP$_L$ operons (R. Crowl et al., "Versatile Expression Vectors for High-Level Synthesis of Cloned Gene Products in *Escherichia Coli*", Gene, 38:31-38 (1985)) in *E. coli* and have been used for the regulation of gene expression in recombinant cells. The corresponding repressors are the lac repressor, trpR and cI, respectively.

Repressors are protein molecules that bind specifically to particular operators. For example, the lac repressor molecule binds to the operator of the lac promoter-operator system, while the cro repressor binds to the operator of the λP$_R$ promoter. Other combinations of repressor and operator are known in the art. See, e.g., J. D. Watson et al., *Molecular Biology Of The Gene*, p. 373 (4th ed. 1987). The structure formed by the repressor and operator blocks the productive interaction of the associated promoter with RNA polymerase, thereby preventing transcription. Other molecules, termed inducers, bind to repressors, thereby preventing the repressor from binding to its operator. Thus, the suppression of protein expression by repressor molecules may be reversed by reducing the concentration of repressor (depression) or by neutralizing the repressor with an inducer.

Analogous promoter-operator systems and inducers are known in other organisms. In yeast, the GAL10 and GAL1 promoters are repressed by extracellular glucose, and activated by addition of galactose, an inducer. Protein GAL80 is a repressor for the system, and GAL4 is a transcriptional activator. Binding of GAL80 to galactose prevents GAL80 from binding GAL4. Then, GAL4 can bind to an upstream activation sequence (UAS) activating transcription. See Y. Oshima, "Regulatory Circuits For Gene Expression: The Metabolisms Of Galactose And Phosphate" in *The Molecular Biology Of The Yeast Sacharomyces, Metabolism And Gene Expression*, J. N. Strathern et al. eds. (1982).

Transcription under the control of the PHO5 promoter is repressed by extracellular inorganic phosphate, and induced to a high level when phosphate is depleted. R. A. Kramer and N. Andersen, "Isolation of Yeast Genes With mRNA Levels Controlled By Phosphate Concentration", *Proc. Nat. Acad. Sci. U.S.A.*, 77:6451–6545 (1980). A number of regulatory genes for PHO5 expression have been identified, including some involved in phosphate regulation.

Mat$e\alpha 2$ is temperature regulated promoter system in yeast. A repressor protein, operator and promoter sites have been identified in this system. A. Z. Sledziewski et al., "Construction Of Temperature-Regulated Yeast Promoters Using The Mat$\alpha 2$ Repression System", *Bio/Technology*, 6:411–16 (1988).

Another example of a repressor system in yeast is the CUP1 promoter, which can be induced by $Cu^{+2}$ ions. The CUP1 promoter is regulated by a metallothionine protein. J. A. Gorman et al., "Regulation Of The Yeast Metallothionine Gene", *Gene*, 48:13–22 (1986).

Inducible promoter systems are also known for mammalian cells. The best known are the $\beta$ interferon promoter, heat shock promoter, metallothionine promoter, and glucocorticoid inhibition system. See generally, R. J. Kaufman, "High Level Production Of Proteins In Mammalian Cells", in *Methods Of Enzymology*, (1987).

In *E. coli*, certain limitations of known expression control system have become apparent. As previously mentioned, expression of product proteins is often deleterious to the host. Known expression control systems do not provide adequate control of bacterial promoters over a wide range of copy numbers, and the amount of product protein expressed after induction may be poor. In the temperature-sensitive promoter systems, for example, protein degradation and aggregation may be increased by the temperature manipulations required to induce the system. Accordingly, there is a need for improved expression control systems for production of product protein in transformed unicellular hosts.

Because transcription is initiated at a promoter, and further because transcription occurs in a 5'→3' direction along a DNA strand, structural genes located 3' to a promoter, but 5' to a termination signal will be subject to control by the same promoter operator. This commonality of transcriptional control defines an operon. The techniques of recombinant DNA technology permit the structural gene for a product protein and, if desired, other genes to be fused with a selected promoter-operator pair to produce a synthetic operon.

FIG. 1, Constructs I–IV depict possible genetic constructs in which transcription of the repressor of product gene transcription is either constitutive or autoregulated. In the latter case, synthesis of the repressor may be under the control of a promoter-operator pair distinct from the operon that includes the structural gene for the product protein, [FIG. 1, Construct III] or may be within the same operon. [FIG. 1, Construct IV].

In genetic constructs referred to herein as "cross-regulation", transcription of the structural gene for a product protein is controlled by a repressor (R) whose transcription is controlled by another promoter-operator system. The repressor of the second operon is designated R2. Four constructs are possible. In the first two [FIG. 1, Constructs V and VI], R2 is under autogenous control. That is, the structural gene encoding the repressor of the second operon is within an operon regulated by it. The second operon also includes a structural gene encoding a repressor (R) of the first operon. The first operon includes the structural gene for the product protein.

In the remaining constructs [FIG. 1, Constructs VII and VIII], the structural gene encoding the product protein as well as the structural gene for R2, the repressor of the second operon, are within a first operon controlled by R. R2 is a repressor molecule that controls transcription within the second operon, including the structural gene for the repressor of the first operon, R. As in earlier examples, the second operon may be located on the host chromosome or on the plasmid harboring the transforming sequences.

Some of these constructs occur in nature. For example, lac repressor synthesis is constitutive, and is analogous to Construct I of FIG. 1. As we show in Example 1, this arrangement has the disadvantage that it is not possible to maintain control of transcription at high copy numbers. That is, when used with plasmids propagated at high copy numbers, transcription of the product gene, and hence product expression, occurs prior to addition of inducer. Alternatively, placing the gene coding for repressor in plasmids harboring the transforming sequences leads to low expression levels even after induction because of overexpression of repressor. [FIG. 1, Construct II] Transcription of the trpR and cI genes in nature is regulated by autorepression—the operon encodes its own repressor. [FIG. 1, Construct III].

We have found that expression of product protein by transformed unicellular hosts is improved by cross-regulation according to the present invention. In particular, when structural genes for repressors of first and second operons are within different operons, with the structural gene for the product protein within a first operon, synthesis of product protein is effectively suppressed until repression of the operator of the first operon is released. Thereafter, expression of product protein occurs at a high rate. Control of the operon containing the structural gene for the product protein is maintained notwithstanding the high copy number. A particularly preferred embodiment of our invention is Construct VIII of FIG. 1, wherein first and second operons are located on plasmids.

The expression of product protein by transformed hosts may be controlled according to this invention. Hosts should be transformed according to Construct VIII of FIG. 1, then propagated to the desired density. Thereafter, control of the first operon is removed, either by decreasing the concentration of repressor (derepression) or by addition of an inducer. Finally, the product protein is harvested.

EXAMPLE 1—Models Of Cross-Regulation

Modeling the synthesis of product protein in the foregoing eight constructs, employing mathematical descriptions of the behavior of transformed bacterial cells and experimentally observed parameters, demonstrates that Construct VIII of FIG. 1 produces optimal results. Control of transcription prior to induction is maintained over a range of copy numbers, while protein product is produced at the greatest rate upon induction.

For this Example, numerical calculations were performed using mathematical descriptions for the behavior of *E. coli* wherein transcription of the structural gene encoding product protein is under the control of the lac promoter-operator system, and wherein the second operon is controlled by the $\lambda P_R$ system. These calculations were based on models of the components involved which have previously been extensively and successfully tested relative to experimental data. See, e.g., Lee, S. B. and Bailey, J. E., "Genetically Structured Models For lac Promoter-Operator Function In The Chromosome And In Multicopy Plasmids: lac Operator Function", *Biotechnology and Bioengineering*, 26:1372–82 (1984); Lee, S. B. and Bailey, J. E., "Genetically Structured Models For lac Promoter-Operator Function In The Chromosome And In Multicopy Plasmids: lac Promoter Function", *Biotechnology and Bioengineering*, 26:1383–89 (1984). For detailed explanation of the mathematical methods used, see W. Chen, J. E. Bailey and S. B. Lee, "Molecular Design Of Expression Systems: Comparison Of Different Repressor Control Configurations Using Molecular Mechanism Models", *Biotechnology and Bioengineering*, 38:679–687 (1991).

Figure 3:
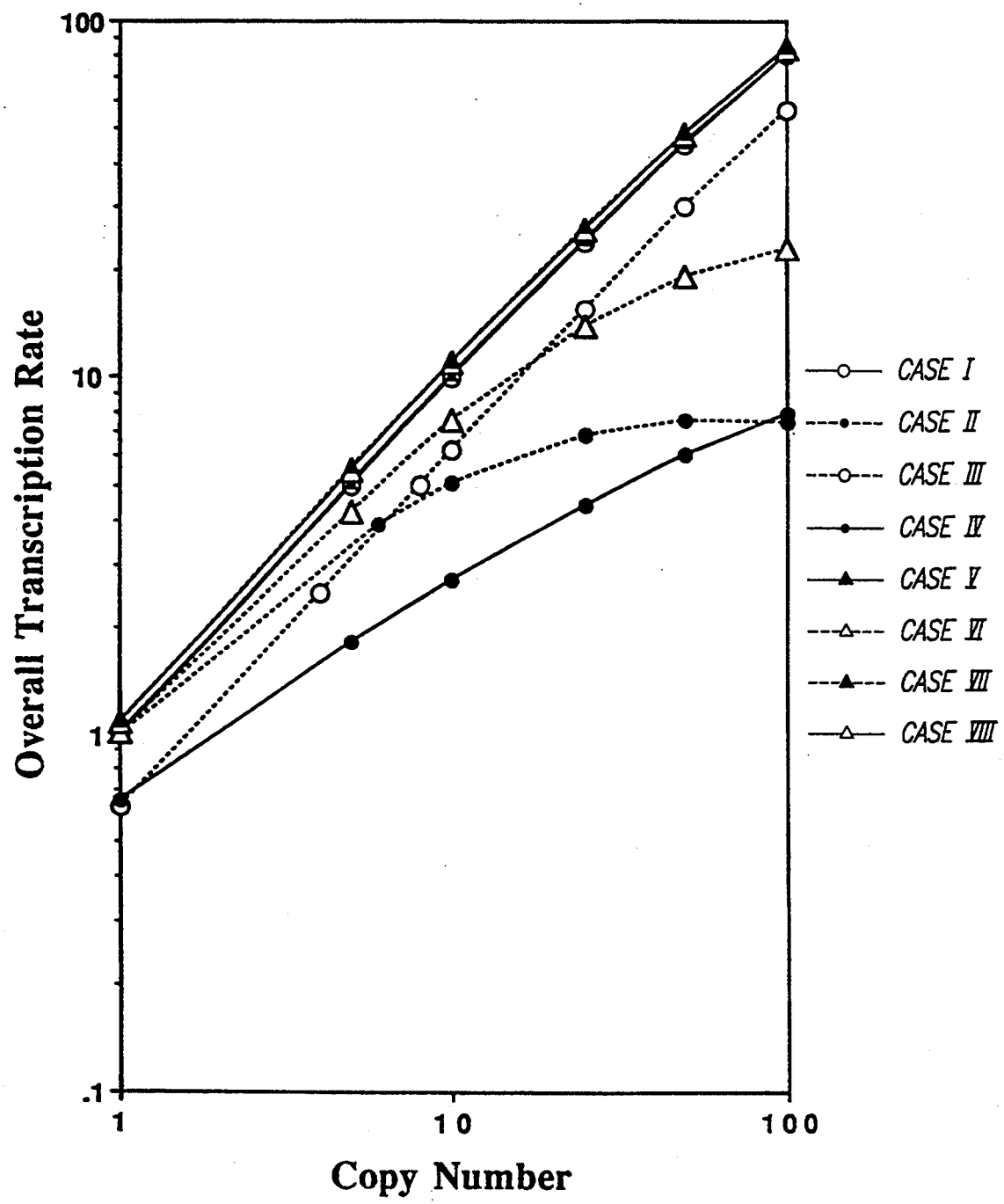
FIG. 3 is a plot of the rate of overall transcription rate for the eight constructs of FIG. 1 after induction.
Figure 4:
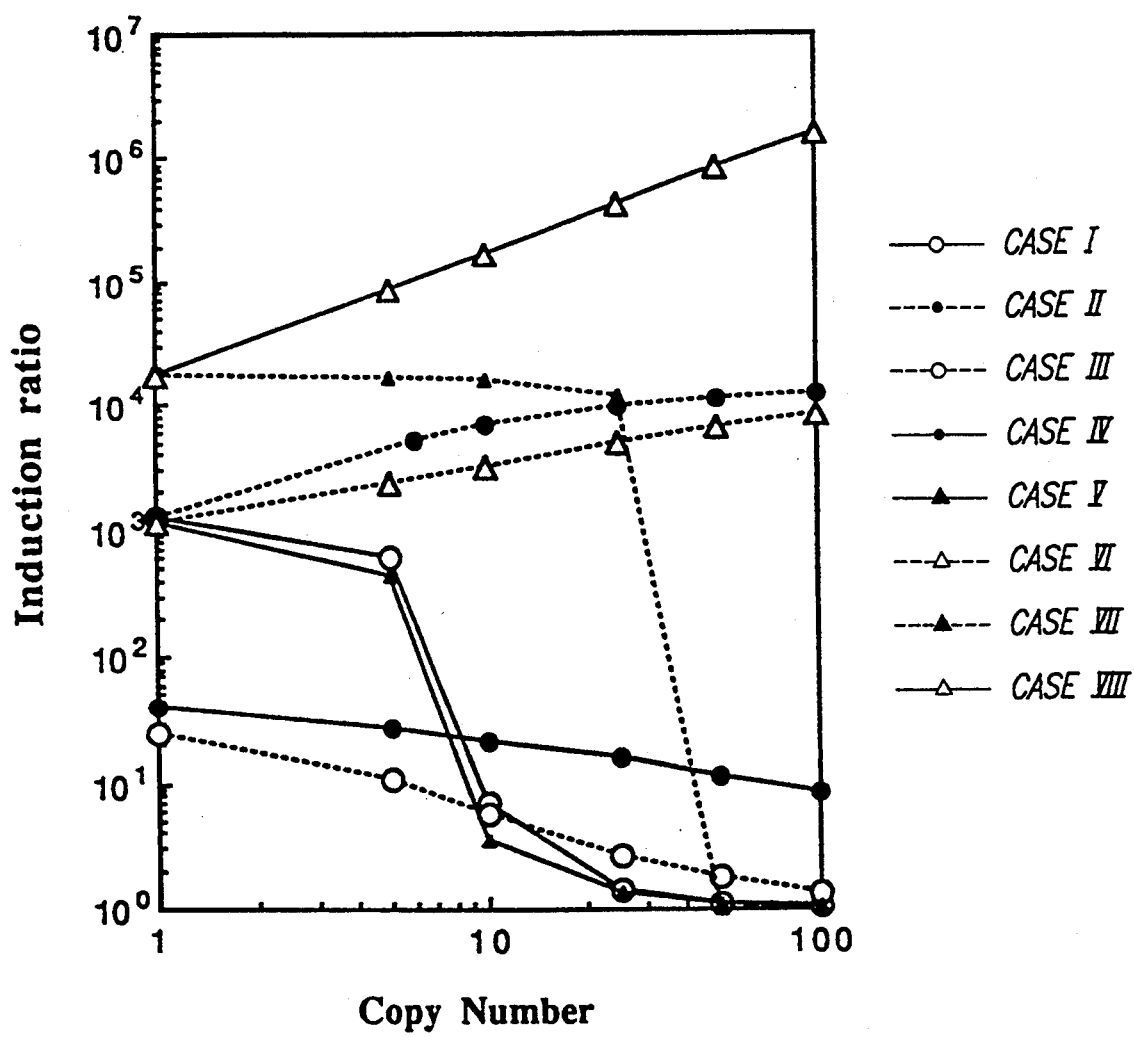
FIG. 4 shows the induction ratio—transcription efficiency (induced)/transcription efficiency (uninduced)—for the eight constructs of FIG. 1.

The aim of the modeling experiments was to determine the effect of the various structural arrangements for controlling the rate of transcription of the product gene over different gene copy numbers. Differences in the copy number of structural genes for product protein could arise due to use of different plasmids as mentioned earlier, or to a change in culture growth rate (see, for example, J. H. Seo and J. E. Bailey, "Effects of Recombinant Plasmid Content on Growth Properties and Cloned Gene Product Formation in *Escherichia coli*", *Biotechnology and Bioengineering*, 27:1668 (1985). The results shown in FIGS. 2 through 4 show expected results at steady state.

A. Uninduced or Repressed Conditions

We calculated "transcription efficiency" a function of the occupancy of the operator site by repressor molecules, as a proxy for the rate of transcription. The rate of transcription is governed by the frequency with which transcription is initiated by RNA polymerase at the promoter. Initiation of transcription is blocked by occupancy of the operator site by a repressor. Hence the frequency with which transcription is initiated, and therefore the overall rate of transcription, is a function of the probability that the operator is occupied by repressor (transcription efficiency).

Figure 2:
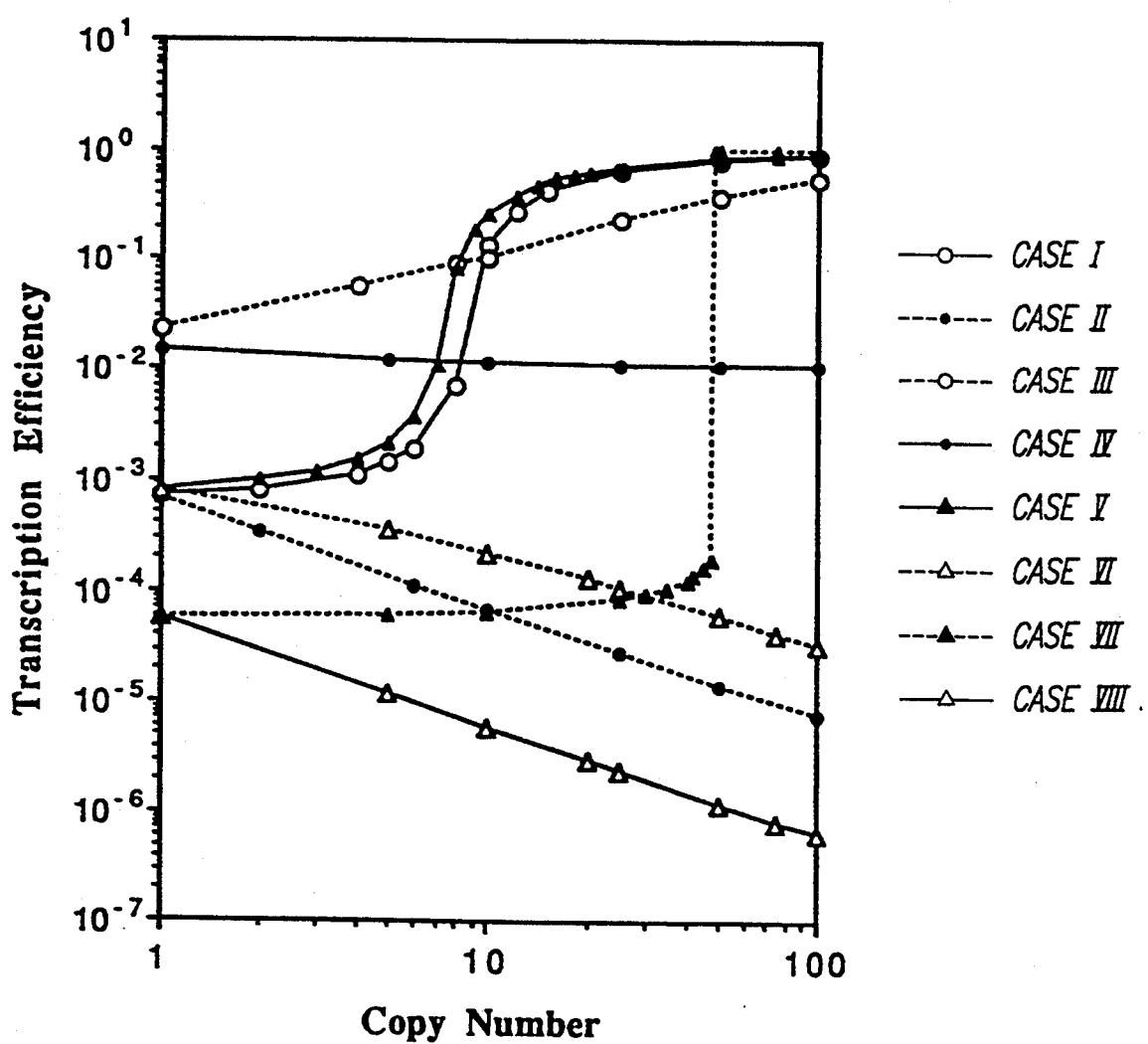
FIG. 2 is a plot of transcription efficiency against copy number for the eight genetic constructs of FIG. 1 during growth phase (prior to induction).

FIG. 2 plots transcription efficiency against copy number for the eight constructs depicted in FIG. 1. For Constructs I through IV of FIG. 1, only one repressor is provided by constitutive expression of a chromosomal repressor gene, regulation of the operon including the gene for the product protein is lost with increasing copy number. For Construct II, in which repressor synthesis is also constitutive, the gene encoding repressor is present on the plasmid that also includes the structural gene for the product protein. In Construct II, transcription efficiency decreases with increasing copy number.

When repressor regulates its own promoter-operator in a chromosomal gene (Construct III), there is a modest loss of control with increasing copy number. If the repressor controls its own synthesis but the repressor gene is located on the plasmid within the operon containing the gene for the product protein, transcription efficiency is essentially independent of copy number (Construct IV).

In Constructs V through VIII, our quantitative model is based on a bacterial system in which expression of the lac repressor (R) is under the control of the $\lambda P_R$ promoter-operator. R2 is cro, the repressor of the $\lambda P_R$ system.

In Constructs V and VI, transcription of both repressors is under the control of the $\lambda P_R$ system; in Construct V, the latter operon is on the chromosome, while in Construct VI, it is located on a plasmid that also harbors an operon that includes the structural gene encoding the product protein.

In Constructs VII and VIII, the structural genes for the product protein and for the repressor of a second operon, R2, are within a first operon. Transcription of the structural genes of the first operon are controlled by repressor R, which is encoded by a structural gene in the second operon. In Construct VII, the first operon is located on a chromosome, while in Construct VIII, both operons are located on a plasmid.

We examined predicted transcription in cross-regulation constructs as a function of increasing copy number. In Construct V, control is suddenly lost beyond a critical copy number. In Construct VI, control is maintained over the entire range of copy numbers, with decreasing transcription efficiency. In Construct VII, control is also lost beyond a critical copy number, while in Construct VIII, control is maintained over the range of copy numbers, with decreasing transcription efficiency.

B. Induced Condition

For these calculations, we assumed that an inducer of the lac operator, isopropylthiogalactoside (IPTG), was present at a concentration of $10^{-3}$M. The overall rate of transcription is plotted against copy number in FIG. 3. Here, except for Construct II, the rate of transcription increases with copy number. Significantly, the rate of transcription is highest for Constructs VII and VIII. The addition of inducer is expected to cause increases in transcription not only of the product but also of the repressor of the second operon, $R_2$. This represses expression of the repressor of the first operon, R, thereby further releasing the promoter of the first operon from repression by R (derepression), and increasing transcription of the structural gene for product protein.

Finally, when the ratio of the calculated transcription efficiencies for the induced and uninduced conditions are compared for all eight Constructs [FIG. 4] as a function of copy number, Construct VIII shows the highest calculated effect of induction on transcription, and further shows that the effect increases with copy number.

Of the eight possibilities compared, Constructs VII and VIII are preferred. Construct VIII maintains control over the full range of copy numbers in the uninduced state, and has the highest overall transcription rate in the induced state.

While our modeling experiments employed numerous parameters available from extensive prior experiments on *E. coli*, we believe our results are generalizable to other hosts and vectors. Thus, while the experimental confirmation of our prediction of the advantages of cross-regulation has been made in a bacterial system, we do not believe that our invention is limited to bacterial hosts.

EXAMPLE 2—Comparison of Constitutive and Cross-regulation of Gene Expression

We examined the expression of a product protein in bacteria in order to compare cross-regulation according to this invention with a regulatory mechanism that occurs in nature. In particular, we compared constitutive regulation (FIG. 1, Construct II) with an example of cross-regulation, wherein the first operon is located on a plasmid (FIG. 1, Construct VIII). In this experiment, the product protein was chloramphenicol acetyltransferase (CAT). The two promoter-repressor systems used were tac-lacI and the $\lambda P_L$-cI. The tac promoter was used to control expression of the CAT protein. In the organisms used to examine control by cross-regulation, the expression of the lac repressor was controlled by the $\lambda P_L$ promoter.

A. Construction of a Cross-Regulation Vector for the Production of CAT Protein

1. Bacteria and plasmids

*E. coli* DH5α (F-, endA1, hsdR17($r_k$-$m_k$+), supE44, thi-1, λ-, recA1, gryA96, relA1, Φ80dlaczAm15) was obtained from BRL (Bethesda Research Laboratories) and was used as the host strain for the plasmid. Different copy number plasmids pRSF1050, pDM246, pDM247, pDM248, and pFH118 were constructed as previously described. See D. R. Moser and J. L. Campbell, 1983, "Characterization and Complementation of pMB1 Copy Number Mutants: Effect of RNA1 Gene Dosage on Plasmid Copy Number and Incompatibility", *J. Bacteriol*, 154:809–818). Plasmid pTCAT, containing a tac-CAT fusion site suitable for this study, was constructed by inserting the HindIII—HindIII CAT fragment from plasmid pCM7 (Phamacia) into the HindIII cut site of pKK223-3. Plasmid pMJR1560 (Amersham) was used as the source for the lacI gene. The cI gene was obtained from pKB252 (Beckman and Ptashne, 1978, "Maximizing Gene Expression on a Plasmid Using Recombination in Vitro", *Cell*, 13, 65–71 1978). Plasmid pSL1180 (Pharmacia) which carried a super polylinker was used for most of the subcloning steps. Plasmid pPL-Lambda (Phamacia) was used as the source of the $\lambda P_L$ promoter.

2. Chemicals, Reagents, and DNA Manipulations

All restriction endonucleases and modifying enzymes (T4 DNA polymerase, Klenow fragment, T4 DNA Ligase, Proteinase K) were purchased from New England BioLabs or Boehringer Mannheim Biochemicals. $^{14}$C-labeled butyryl coenzymeA was obtained from New England Nuclear. All DNA manipulations were done according to standard methods (Maniatis et al. "Molecular Cloning, A Laboratory Manual, 2nd ed. Cold Spring Harbor Laboratory, Cold Spring Harbor (1990)). DNA fragments were eluted from agarose gels using a Geneclean Kit (Bio 101).

3. Synthesis of lacI and cI Structural Genes

The polymerase chain reaction (PCR) technique is generally used to amplify a segment of DNA that lies between two regions of known DNA sequence. Two oligonucleotides are used as primers for a series of extension reactions that are catalyzed by the Taq DNA polymerase (Cetus) enzyme, which is thermally stable. These primers are complementary to sequences on the opposite strands of the template DNA and flank the segment of DNA that is to be amplified. The template DNA is first denatured by heating to a high temperature in the presence of excess primers and the four deoxynucleotidetriphosphates (dNTP). Thereafter, the primers are allowed to annealed to their target sequence during cooling of the reaction mixture, after which the annealed primers are extended. Because the products of one round of amplification serve as templates for the next, the amount of sequence sought are thus amplified exponentially.

This technique was used to synthesize both the lacI and cI structural gene using plasmid pMJR1560 (Amersham) and plasmid pKB252 (obtained from M. Ptashne) as templates, respectively. Primers I (SEQ. ID NO. 1) and II (SEQ. ID No. 2) (FIG. 5) were used to amplify the lacI gene. The native lacI transcriptional termination signal, which overlaps the lac promoter region was replaced by a-strong trpA transcriptional termination signal as indicated in FIG. 2. In addition, an extra translational stop codon was inserted in frame after native stop codon to ensure effective translational stop. The Shine-Delgarno sequence (S-D) for the lacI gene was also included in primer I (SEQ. ID No. 1) BspEI sites were created at both ends of the primers to facilitate subcloning of the amplified PCR fragment.

To synthesize the structural gene of the cI repressor, primers III (SEQ. ID No. 3) and IV (SEQ. ID No. 4) were used (FIG. 6). The S-D sequence and the transcriptional termination signal were not included in these primers because they are provided by the vector used for subcloning the amplified cI fragment. Restriction sites EcoRI and PstI were created at the 5' end of primer III (SEQ. ID No. 3) and IV (SEQ. ID No. 4), respectively.

The PCR reaction was carried out in a 50 μL final reaction volume containing 2.5 μL of a 1 to 25 dilution of each respective template DNA, 5 μL of 10×reaction buffer (100 mM Tris-HCl pH 8.3, 500 mM KCl, 15 mM MgCl$_2$, 0.01% (W/V) gelatin), 8 μL of dNTPs mix (1.25 mM each), 2 μL each of the primers, and 0.5 μL of Taq DNA polymerase (Cetus). The amplification reaction was carried out for 36 cycles in a DNA thermal cycler (Perkin Elmer-Cetus). The DNA was denatured at 92° C. for 1 min, annealed at 42° C. for 2 min, and extended at 72° C. for 3 min. The amplified products were analyzed on a 1.2% agarose gel in order to verify that they have the correct size.

4. Construction of a Cross-Regulation Plasmid

Plasmid pKC2 was constructed by inserting a 1.5 kb BspHI fragment from pTCAT containing the tac-CAT fusion into the corresponding complimentary NcoI site in plasmid pSL1180 (Pharmacia). The resulting plasmid retained the entire tac-CAT fusion including the strong rrnB termination sequence (this sequence is included in plasmid pKK223-3) but did not extend into the ampicillin resistance gene region.

The 736 bp cI fragment obtained from PCR amplification was purified using the Geneclean kit (Bio101), digested with EcoRI and PstI nucleases, and ligated into plasmid pKQV4 (Strauch M. A., essentially the same as pKK223-3 except it contained the lacIQ gene isolated from pMJR1560) previously opened with the same enzymes. The resulting plasmid pTCI carried the cI gene under the control of the tac promoter. Primer III (SEQ. ID No. 3) used for the synthesis of this cI fragment was designed such that the distance between the start codon of the cI gene and the ribosome binding site (SD sequence) on the plasmid was 10 base pairs in length. Plasmid pSIAT was derived by replacing a 622 bp MluI-PstI fragment carrying the entire tac promoter from pKC2 by a 922 bp BamHI-PstI fragment containing the tac-cI fusion with the MluI-BamHI end rendered blunt by filling in, using the Klenow fragment of DNA polymerase, thus creating a tac-cI-CAT operon. Both BamHI and MluI sites were regenerated after ligation.

The lacI PCR product was isolated on a 1.2% agarose gel and purified with a Geneclean kit. Proteinase K treatment was used to the purified DNA. It was then subjected to phenolchloroform extraction and ethanol precipitation. This purified 1169 bp lacI fragment was then ligated into the unique SmaI site of pUC18 to give pUC18-lacI. To construct pλ-lacI, a 1.2 kb lacI fragment was cleaved with EcoRI/SphI and inserted into the BspEI/SphI sites of pPL-Lambda (Pharmacia) with blunt end ligation at the EcoRI-BspEI site (both ends were made blunt by filling in with Klenow.

Plasmids pλ-lacI and pSIAT were cleaved with NruI/BamHI and a 1.9 kb fragment from pλ-lacI was inserted into pSIAT, replacing the smaller fragment from the latter to yield pKC7. The resulting construct has the tac-cI-CAT operon and the $\lambda P_L$-lacI fusion facing in the opposite orientation. That configuration ensured that the expression of these genes would be strictly under control of their own promoters. Furthermore, since transcription termination signals were included at the 3' end of the gene, no transcripts initiated within the plasmid can extend into this region. To transfer the expression cassette into the different copy number plasmids, pKC7 was digested with BstBI and SphI and a 3.7 kb fragment carrying the entire cross-regulation system was ligated into the SacI and SphI sites (2.7 kb of nonessential DNA was removed with these cleavages) of plasmids pDM246, pDM247, pDM248, pRSF1050, and pFH118 (See D. R. Moser and J. L. Campbell, 1983), supra, to give pC8246, pC8247, pC8248, pC81050, and pC8118, respectively with blunt end ligation at the BstBI-SacI end.

B. Comparison Of CAT Synthesis For The Constitutive (II) And Cross-Regulation (VIII) Constructs CAT expression by strains DH5α/pKC6 (Construct II) and DH5α/pKC7 (Construct VIII) were compared. Vector pKC6 was derived from pSL1180 containing the lacI$^Q$ gene and the tac-CAT fusion facing in opposite directions. Since plasmids pKC7 and pKC6 contained the same replication origin, they are expected to have the same copy number.

1. Media and cell growth

Transformed cells in 5 mL of inoculum were grown overnight at 37° C. in LB medium (10 g/L tryptone, 5 g/L yeast extract, 10 g/L NaCl, 3 g/L $K_2HPO_4$, and 1 g/L $KH_2PO_4$). 1.5 mL of the overnight culture was added to 50 mL of LB medium and cells were grown at 37° C. until stationary phase. Ampicillin was added to a concentration of 50 mg/L for selection. Cell growth was followed by measuring the optical density at 660 nm with a Spectronic 21 spectrophotometer (Milton Roy). IPTG was added to induce CAT production.

2. CAT and protein assay

Cells were disrupted by sonication. The soluble fraction was assayed with $^{14}$C-labeled butyryl coenzyme A (New England Nuclear) according to recommended protocols, B. M. Newman et al., "A Novel Rapid Assay for Chloramphenicol Acetyltransferase Gene Expression, *Biotechniques*, 5:444–447 (1987). To carry out the assay, 1 μL of cell extract was added to a 7 mL glass miniscintillation vial (Kimble) containing sufficient 100 mM Tris-HCl (pH 7.8) to give a total volume of 50 μL.200 μL of freshly prepared 1.25 mM chloramphenicol in 100 nM Tris-HCl (pH 7.8), followed by addition of 1 μci of $^{14}$C-Butyryl CoA. 5 mL of a scintillation fluor (Econofluor) was gently overlaid on top of the reaction mixture. The vial was counted in a liquid scintillation counter (Beckman model LS5801) and the CAT activity was calculated from the slope of the cpm versus incubation time plot. CAT activity was expressed in units of CAT per milligram of total soluble protein. Total protein was determined with the same fraction by using a protein assay kit (Sigma).

3. Results

FIG. 7 shows the growth curves (circles) and specific CAT activity (squares) for both strains. Before the addition of IPTG, both strains show a low level of CAT activity with that of pKC7 slightly lower than pKC6. Upon induction by the addition of IPTG, the CAT activity increases significantly. However, the CAT activity for pKC6 (solid squares) eventually stabilized while that for pKC7 continued to increase to approximately two times the activity of pKC6 3 hours after addition of inducer (open squares). Measurement of O.D. in the respective cultures (circles) demonstrates that the differences in enzyme production cannot be explained by differences in cell density.

Results from this experiment match well with our modelling results, demonstrating excellent control of expression prior to induction and higher expression post-induction for the cross-regulation construct.

While we have presented a number of embodiments of this invention by way of examples, it is apparent that our basic construction can be altered to provide other embodiments that also employ our invention. The scope of our invention is defined by the scope of the Claims, rather than by the examples, which are only intended to be illustrative.

We claim:

1. A transformed unicellular host, selected from the group consisting of *Escherichia coli* and *Saccharomyces cerevisiae*, said unicellular host transformed with a dual expression construct, said dual expression construct having a first expression construct and a second expression construct, said first expression construct comprising a first operator and a first promoter, both operably linked to a structural gene encoding a product protein and to a structural gene encoding a first repressor; said second expression construct comprising a second operator and a second promoter, both operably linked to a structural gene encoding a second repressor, said first repressor repressing transcription of the gene encoding said second repressor through binding of said first repressor to said second operator, said second repressor suppressing transcription of the gene encoding the product protein in the first expression construct through binding of said second repressor to said first operator.

2. The transformed host of claim 1 wherein the transformed host is *Escherichia coli* and at least one promoter is selected from the group consisting of the lac promoter, the trp promoter, the tac promoter, $\lambda P_r$ and $\lambda P_L$.

3. The transformed host of claim 1 wherein the transformed host is *Saccharomyces cerevisiae* and at least one promoter is selected from the group consisting of the GAL10 promoter, the GAL1 promoter, the PHO5 promoter, the, MATα2 promoter and the CUP1 promoter.

4. The transformed unicellular host of claim 1 wherein the second expression construct is located on a chromosome and the first expression construct is located on a plasmid.

5. The transformed unicellular host of claim 1 wherein the first and second expression construct are located on a plasmid.

6. The transformed unicellular host of claim 5 wherein the first and second operons are located on the same plasmid.

7. The transformed unicellular host of claim 1 wherein the transformed host is *Escherichia coli* and the first repressor is selected from the group consisting of lacI, cro, cI and trpR.

8. The transformed host of claim 1 wherein the transformed host is *Escherichia coli* and the promoters are selected from the group consisting of the lac system, the tac system, $\lambda P_r$ and $\lambda P_L$.

9. The transformed host of claim 1 wherein the transformed host is *Saccharomyces cerevisiae* and the promoters are selected from the group consisting of GAL10, GAL1, PHO5, Matα2 and CUP1.

10. A method for controlling the expression of a product protein by a transformed unicellular host, selected from the group consisting of *Escherichia coli* and *Saccharomyces cerevisiae*, wherein the host is transformed by a dual expression construct, said dual expression construct having a first expression construct and a second expression construct, said first expression construct comprising a first operator and a first promoter, both operably linked to a structural gene encoding a product protein and to a structural gene encoding a first repressor; said second expression construct comprising a second operator and a second promoter, both operably linked to a structural gene encoding a second repressor, said first repressor repressing transcription of the gene encoding said second repressor through binding of said first repressor to said second operator, said second repressor repressing transcription of the gene encoding the product protein in the first expression construct through binding of said second repressor to said first operator, comprising the steps of:
  a) transforming the unicellular host with at least one plasmid which includes the dual expression construct;
  b) reducing the repression of transcription of the gene encoding the product protein; and
  c) collecting the product protein.

11. The method of claim 10 wherein the step of reducing is effected by reducing the concentration of a repressor of the expression construct that includes the gene encoding the product protein.

12. The method of claim 10, wherein the step of reducing repression of transcription of the gene encoding the product protein is effected by an inducer.

13. The method of claim 12 wherein the host is *Escherichia coli* and the inducer is isopropylthiogalactoside.

14. The method of claim 11 wherein the host is *Escherichia coli* and the repressor is selected from the group consisting of lacI, cro, cI and trpR.

15. The method of claim 12 wherein the host is *Saccharomyces cerevisiae*, the promoters are selected from the group consisting of the GAL10 promoter and the GAL11 promoter, and the inducer is galactose.

* * * * *

SEQUENCE LISTING ( 1 ) GENERAL INFORMATION:

( i i i ) NUMBER OF SEQUENCES: 4

( 2 ) INFORMATION FOR SEQ ID NO: 1:

( i ) SEQUENCE CHARACTERISTICS:
( A ) LENGTH: 40
( B ) TYPE: nucleic Acid
( C ) STRANDEDNESS: single stranded
( D ) TOPOLOGY: linear ( i i ) MOLECULE TYPE: cDNA to genomic DNA
    ( A ) DESCRIPTION: Primer for PCR amplification ( i i i ) HYPOTHETICAL: no ( i v ) ANTI-SENSE: no ( v ) FRAGMENT TYPE: n/a ( v i ) ORIGINAL SOURCE: synthetic ( v i i ) IMMEDIATE SOURCE: synthetic ( v i i i ) POSITION IN GENOME: n/a ( i x ) FEATURE: primers for PCR amplification of lacI gene ( x ) PUBLICATION INFORMATION:

( x i ) SEQUENCE DESCRIPTION: SEQ ID. NO: 1:

```
        GCGATTCCGG ATTAGCAATT CAGGGTGGTG AATGTGAAAC       40
```

( 2 ) INFORMATION FOR SEQ ID NO:2:

( i ) SEQUENCE CHARACTERISTICS:
        ( A ) LENGTH: 75
        ( B ) TYPE: nucleic Acid
        ( C ) STRANDEDNESS: single stranded
        ( D ) TOPOLOGY: linear ( i i ) MOLECULE TYPE: cDNA to genomic DNA
        ( A ) DESCRIPTION: Primer for PCR amplification ( i i i ) HYPOTHETICAL: no ( i v ) ANTI-SENSE: no ( v ) FRAGMENT TYPE: n/a ( v i ) ORIGINAL SOURCE: synthetic ( v i i ) IMMEDIATE SOURCE: synthetic ( v i i i ) POSITION IN GENOME: n/a ( i x ) FEATURE: primers for PCR amplification of lacI gene ( x ) PUBLICATION INFORMATION:

( x i ) SEQUENCE DESCRIPTION: SEQ ID. NO: 2:

```
        GCTAATCCGG AATCGCAAAA AAAAGCCCGC TCATTAGGCG       40
        GGCTGCGTTA CGCTCACTGC CCGCTTTCCA GTCGG            75
```

( 2 ) INFORMATION FOR SEQ ID NO:3:

( i ) SEQUENCE CHARACTERISTICS:
        ( A ) LENGTH: 47
        ( B ) TYPE: nucleic Acid
        ( C ) STRANDEDNESS: single stranded
        ( D ) TOPOLOGY: linear ( i i ) MOLECULE TYPE: cDNA to genomic DNA
        ( A ) DESCRIPTION: Primer for PCR amplification ( i i i ) HYPOTHETICAL: no ( i v ) ANTI-SENSE: no ( v ) FRAGMENT TYPE: n/a ( v i ) SOURCE: synthetic ( v i i ) IMMEDIATE SOURCE: synthetic ( v i i i ) POSITION IN GENOME: n/a

```
    ( i x ) FEATURE: primers for PCR amplification of cI genes ( x ) PUBLICATION INFORMATION:

( x i ) SEQUENCE DESCRIPTION: SEQ ID. NO: 3:

GGGAATTCAT  GAGCACAAAA  AAGAAACCAT  AGGAAACAGA         40

ATTCATG                                                47

( 2 ) INFORMATION FOR SEQ ID NO:4:

( i ) SEQUENCE CHARACTERISTICS:
            ( A ) LENGTH: 30
            ( B ) TYPE: nucleic Acid
            ( C ) STRANDEDNESS: single stranded
            ( D ) TOPOLOGY: linear ( i i ) MOLECULE TYPE: cDNA to genomic DNA
            ( A ) DESCRIPTION: Primer for PCR amplification ( i i i ) HYPOTHETICAL: no ( i v ) ANTI-SENSE: no ( v ) FRAGMENT TYPE: n/a ( v i ) ORIGINAL SOURCE: synthetic ( v i i ) IMMEDIATE SOURCE: synthetic ( v i i i ) POSITION IN GENOME: n/a ( i x ) FEATURE: primers for PCR amplification of cI gene ( x ) PUBLICATION INFORMATION:

( x i ) SEQUENCE DESCRIPTION: SEQ ID. NO: 4:

GCTGCAGCTT  ATCAGCCAAA  CGTCTCTTCA         30
```